United States Patent [19]

McClure et al.

[11] 4,052,475
[45] Oct. 4, 1977

[54] TOLUENE DISPROPORTIONATION PROCESS USING A SUPPORTED PERFLUORINATED POLYMER CATALYST

[75] Inventors: James D. McClure; Stanley G. Brandenberger, both of Houston, Tex.

[73] Assignee: Shell Oil Company, Houston, Tex.

[21] Appl. No.: 783,908

[22] Filed: Apr. 1, 1977

Related U.S. Application Data

[62] Division of Ser. No. 663,956, March 4, 1976.

[51] Int. Cl.$^2$ .................................................. C07C 3/62
[52] U.S. Cl. ............................................. 260/672 T
[58] Field of Search ................................... 260/672 T

[56] References Cited

U.S. PATENT DOCUMENTS

| 3,324,193 | 6/1967 | Bloch et al. | 260/672 T |
| 3,326,866 | 6/1967 | Haag | 260/672 T |

Primary Examiner—Delbert E. Gantz
Assistant Examiner—C. E. Spresser
Attorney, Agent, or Firm—Dean F. Vance

[57] ABSTRACT

A process and catalyst for the disproportionation of toluene is disclosed. The catalyst is a supported solid perfluorinated polymer containing pendent sulfonic acid groups.

7 Claims, No Drawings

TOLUENE DISPROPORTIONATION PROCESS USING A SUPPORTED PERFLUORINATED POLYMER CATALYST

This is a division of application Ser. No. 663,956, filed Mar. 4, 1976.

BACKGROUND OF THE INVENTION

Hydrocarbon conversion and the isomerization of hydrocarbons in particular, is of special importance to the petroleum industry. In recent years, with the advent of catalytic converters in automobiles and the required use of non-leaded gasoline, a need has arisen for higher octane number gasolines. Natural straight-run gasolines, i.e., naphthas, contain, chiefly, normal paraffins, such as normal pentane and normal hexane, which have relatively low octane numbers. It has become essential, therefore, to convert these low octane components to their higher octane counterparts. The isomerization of these hydrocarbon components accomplish this conversion, i.e., the isomers resulting have a much higher octane rating. Hence, the facility with which this isomerization is accomplished has become of prime importance.

Likewise, the need for isoparaffins, benzene, xylene, and ethyl benzene as building components in the petrochemical industry is increasing. Accordingly, the need for improved hydrocarbon conversion processes in the petrochemical industry is also great.

One of the primary hydrocarbon conversion processes now employed is the alkylation of isoparaffins. It was through that certain sulfonated fluorocarbon polymers possess sufficient activity and stability to be useful as alkylation catalysts. However, in a recent study by Kapura and Gates, Sulfonated Polymers as Alkylation Catalysts, Industrial Engineering Chemistry Product Research Development, Vol. 12, No. 1, pp. 62–66 (1973), it was found that a sulfonated fluorocarbon vinyl ether polymer was inactive in alkylating isobutane with propylene in the gas phase and in a mole ratio of 5 to 1 at 260° C. The conclusion reached in that study was that the sulfonated fluorocarbon vinyl ether polymer catalyst was too weakly acidic to catalyze paraffin alkylation and that the polymer was not a useful catalyst. That study also showed that these same ion exchange resins were useful in the alkylation of benzene with propylene in the vapor phase to form cumene. However, the conclusion reached by Kapura and Gates with regard to the formation of cumene was that the sulfonated polymer was not "a particularly useful catalyst at temperatures greater than about 150° C." Contrary to the conclusions reached by Kapura and Gates, it has been found that a supported perfluorinated polymer containing pendant sulfonic acid groups is a very active catalyst in the preparation of ethylbenzene from benzene and ethylene, in the alkylation of isoparaffins, in the isomerization of normal alkanes, and in the disproportionation of toluene.

SUMMARY OF THE INVENTION

The present invention comprises an improved hydrocarbon conversion process which comprises contacting said hydrocarbons under hydrocarbon converting conditions with a supported perfluorinated polymer catalyst containing a repeating structure selected from the group consisting of:

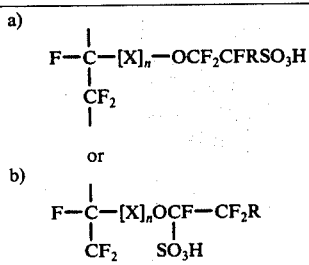

where $n$ is 0, 1 or 2; R is a radical selected from the group consisting of fluorine and perfluoroalkyl radicals having from 1 to 10 carbon atoms; and X is selected from the group consisting of:

$$[O(CF_2)_m], [OCF_2CFY] \text{ or } [OCFYCF_2]$$

where $m$ is an integer from 2 to 10 and Y is a radical selected from the class consisting of fluorine and the trifluoromethyl radical.

Also disclosed is a novel catalyst composition for the conversion of hydrocarbons which comprises a catalytic component dispersed on a solid, porous support. The catalytic component is the perfluorinated polymer having the structure I or II above. The solid porous support has an effective pore diameter of between about 50 A and about 600 A and is preferably selected from the group consisting of alumina, silica, silica-alumina and porous glas.

DETAILED DESCRIPTION OF THE INVENTION

A. The Catalyst Composition

The catalyst employed in the present invention is a solid at reaction conditions. The catalyst broadly comprises a perfluorinated polymer having acid groups in the amount of about 0.01 to 5 mequiv/gram catalyst. Preferably, the polymer contains about 0.05 to 2 mequiv/gram of catalyst.

In a specific embodiment, the polymer catalyst contains a repeating structure selected from group consisting of:

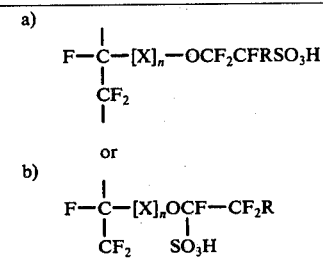

where $n$ is 0, 1 or 2; R is a radical selected from the group consisting of fluorine and perfluoroalkyl radicals having from 1 to 10 carbon atoms; and X is selected from the group consisting of:

$$[O(CF_2)_m], [OCF_2CFY] \text{ or } [OCFYCF_2]$$

where $m$ is an integer from 2 to 10 and Y is a radical selected from the class consisting of fluorine and the trifluoromethyl radical. In a preferred embodiment, $n$ is 1 or 2, Y is a trifluoromethyl radical, R is fluorine, and $m$ is 2. Catalysts of the above-noted structure typically have a molecular weight of between about 1,000 and 500,000 daltons.

Polymer catalysts of the above-noted structure can be prepared in various ways. One method, disclosed in Connolly et al, U.S. Pat. No. 3,282,875 and Cavanaugh et al, U.S. Pat. No. 3,882,093, comprises polymerizing vinyl compounds of the formula:

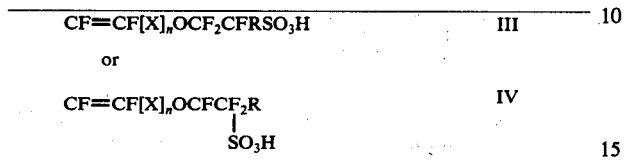

in a perfluorocarbon solvent using a perfluorinated free radical initiator. Since the vinyl ethers are liquid at reaction conditions, it is further possible to polymerize and copolymerize the vinyl ethers in bulk without the use of a solvent. Polymerization temperatures vary from $-50°$ to $+200°$ C depending on the initiator used. Pressure is not critical and is generally employed to control the ratio of the gaseous comonomer to the fluorocarbon vinyl ether. Suitable fluorocarbon solvents are known in the art and are generally perfluoroalkanes or perfluorocycloalkanes, such as perfluoroheptane or perfluorodimethylcyclobutane. Similarly, perfluorinated initiators are known in the art and include perfluoroperoxides and nitrogen fluorides. It is also possible to polymerize the vinyl ethers of structure III or IV in an aqueous medium using a peroxide or a redox initiator. The polymerization methods employed correspond to those established in the art for the polymerization of tetrafluoroethylene in aqueous media.

It is also possible to prepare catalysts for the present invention by copolymerizing the vinyl ethers of structure III or IV with perfluoroethylene and/or perfluoro-alpha-olefins. A preferred copolymer prepared by polymerizing perfluoroethylene with a perfluorovinyl ether containing attached sulfonic acid groups would have the following structure:

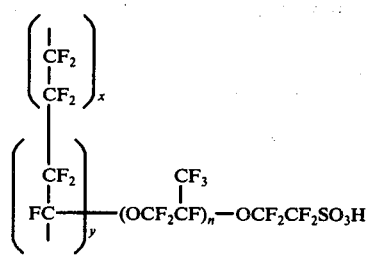

wherein $n = 1$ to 2 and the ratio of $x$ over $y$ varies from about 2 to about 50. The polymer of structure V is available commercially under the tradename of NAFION ® resin. Catalysts of the above-noted structure V offer the advantages of high concentrations of accessible acid groups in a solid phase.

The catalyst of the present invention is supported on a porous solid inert support. The supported catalysts possess greater activity per unit of acid present than do the unsupported catalysts. By porous solid support is meant an inert support material having a porous structure and an average pore diameter of between about 50 A and about 600 A or higher. Preferably, the average pore diameter of the support is greater than about 200

A. The porous solid support of the subject invention is preferably selected from the inorganic oxide group consisting of alumina, fluorided alumina, zirconia, silica, silica-alumina, magnesia, chromia, boria, and mixtures and combinations thereof. Other porous solid supports may also be used such a bauxite, kieselguhr, kaolin, bentonite, diatomaceous earth and the like. Other porous solid supports such as polytetrafluoroethylene, carbon, e.g., charcoal, polytrichlorofluoroethylene, porous glass, and the like may also be used. Basically, the support should be substantially inert to the catalyst, and be insoluble in the mixture under reaction conditions.

The average pore diameter (also known as effective pore diameter) of the support, which is related to the ratio of pore volume to surface area, is an important consideration in the choice of support. Generally, as the average pore diameter of the support is increased, the activity of the catalyst is increased. For example, as shown in the illustrative Embodiments which follow, an isomerization catalyst composition having a porous glass support with a 207 A average pre diameter was only about 60% as active as an isomerization catalyst composition having a porous glass support with a 310 A average pore diameter. Most preferably, the support should possess both a high surface area and a high average pore diameter.

The weight ratio of catalyst to support varies from about 0.1:100 to about 30:100, preferably from about 1:100 to about 15:100. The support is preferably impregnated with the catalyst by dissolving the catalyst in a solvent, such as ethanol, mixing the support and the catalyst solution, and then drying the impregnated support under vacuum at a temperature of between about 25° C and about 100° C so as to remove the solvent.

Disproportionation of Toluene

Recently, with the increase in the production of synthetic fibers, demand for benzene and xylene has increased. Therefore, the so-called disproportionation process for converting toluene to benzene and xylene has been examined for industrial applications. Most of these processes employ Friedel-Crafts catalysts. Other reported processes employ silica-aluminia, alumina-boria, or crystalline zeolites as catalysts. See, e.g., U.S. Pat. No. 3,576,895 and U.S. Pat. No. 3,553,277.

However, most of these known catalysts exhibit only a low catalytic activity for the disproportionation reaction of toluene, and further, these catalysts have such shortcomings as a relative short catalyst life and problems with extreme carbon deposition on the catalyst.

In the present invention, a toluene-containing stream is contacted with a catalyst of the instant invention in the liquid phase and at a temperature of between about 150° C and 225° C. In a preferred embodiment, a hydrogen gas-containing stream is also employed in the reaction.

The toluene feed for the present invention is typically obtained as a refinery process stream from an extraction process. Accordingly, the stream typically contains some benzene and xylene in addition to the toluene. Toluene concentrations of greater than about 50% volume are preferred, however.

The process may be carried out either as a batch or continuous type of operation, although it is preferred to carry out the process continuously. It has generally been established that the more intimate the contact between the feedstock and the catalyst, the better the yield of desired product obtained. With this in mind, the present process, when operated as a batch operation, is characterized by the use of vigorous mechanical stirring or shaking of the reactant and catalyst.

When employing a continuous process, the feedstocks may be contacted with the supported catalyst in any suitable reactor. In one embodiment, the supported catalyst is packed in a vertical, tubular reactor bed with inert supports, such as ceramic balls or silicon carbide, above and below the supported catalyst to prevent entrainment of the solid catalyst. In a further embodiment, the supported catalyst is mixed with an inert material, such as quartz, and loaded in the reactor so as to improve the fluid dynamics of the system. The flow of the reactant feed stream may be upflow or downflow, with an upflow arrangement being preferred to ensure a liquid phase reaction.

Reaction temperature is varied between about 150° C and 225° C. The reaction temperature must be kept about 225° due to the lack of stability of the catalyst at temperatures of over 250° C. A preferred temperature range is between about 175° C and 210° C.

In general, the pressure in the reaction zone is maintained to keep the toluene in liquid phase, and accordingly, will vary with the particular feestock employed and the reaction temperatures. Typical reaction zone pressure varies from about 10 psig to about 2,000 psig.

The weight hourly space velocity effectively measures the catalyst concentration employed, and hence, also measures the relative activity of the catalyst. Weight hourly spaced velocity (WHSV) is defined as the weight per hour of toluene feed divided by the weight of catalyst (not including support) employed. For a non-supported catalyst, the WHSV varies between about 0.05 hr$^{-1}$ to about 1.0 hr$^{-1}$. For a supported catalyst, the WHSV varies from between about 0.5 hr$^{-1}$ to about 10.0 hr$^{-1}$. The larger WHSV employed for supported catalysts is possible because of the greater activity of the supported catalysts.

In a preferred embodiment, a gas stream is introduced into the reaction zone along with the toluene feed stream. Typically, the gas is an inert gas such as nitrogen. However, it has been found that when the gas stream also contains some hydrogen, the conversion of toluene is increased while the production of unwanted products such as $C_3$-$C_5$ cracked gases and non-volatile aromatic products is decreased. A preferred gas composition contains between about 2% to 95% hydrogen with the remainder being an inert gas such as nitrogen. The volume ratio of gas to toluene varies from about 0.5:1 to about 20:1.

The invention is further illustrated by means of the following Comparative Example and Illustrative Embodiments which are given for the purpose of illustration only, and the invention is not to be regarded as limited to any of the specific materials or conditions recited therein.

In the Comparative Example and Illustrative Embodiments, the reactor employed was a 17-inch stainless steel tube equipped with both a liquid feed upflow inlet and a nitrogen inlet. The catalyst bed occupied about 10 inches in the center of the reactor; and on either side of the catalyst bed were packed about 10 grams of caborumdum chips.

In all cases, the reactants were introduced in an upflow manner, pressure was kept at 300 psig to maintain a liquid phase, and the feed stream was 100% toluene. Catalyst concentration is measured by weight hourly spaced velocity (WHSV, hr$^{-1}$) which is defined as the weight of the toluene feed divided by the weight of catalyst (excluding support).

COMPARATIVE EXAMPLE 1D

The catalyst employed in Comparative Example 1d was prepared by grinding Nafion XR granules with a blender to 150 micrometer or less particle size. The ground material was then treated twice with 30% sulfuric acid to convert the material from a potassium (K+) form to the H+ form. The treated material was collected by filtration, washed with distilled water until the washings were neutral, and then dried to 100° C and 3 mm pressure for 16 hours. The resulting catalyst contained about 0.85 milliequivalents of acid per gram of catalyst. The structure for the resulting catalyst is exemplified by the following repeating structure where $n = 1$ or 2 and the ratio of $x$ over $y$ varies from between 2 and about 50:

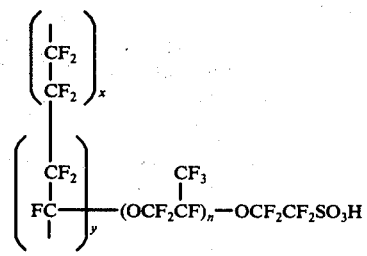

In comparative Example 1d, the catalyst bed comprised 5 grams of the catalyst plus 5 grams of quartz particles. A stream of 100% nitrogen in a volume ratio of 1:1 with the toluene feed was maintained. The WHSV was maintained at 0.43 hr$^{-1}$. The results are presented below in Table 1d.

Table 1d

| Time, hr | 5 | 26 | 46.5 | 68.5 | 72.5 | 91.5 |
|---|---|---|---|---|---|---|
| Temperature, ° C | 200 | 200 | 200 | 200 | 225 | 225 |
| Composition of Product % w | | | | | | |
| $C_3$-$C_5$ | 0.8 | 0.8 | 0.8 | 0.8 | 1.0 | 0.4 |
| Toluene | 78 | 78.5 | 79 | 84 | 84 | 90 |
| Benzene | 9.9 | 9.9 | 9.5 | 7.3 | 7.3 | 4.6 |
| o-Xylene | 2.2 | 2.0 | 1.9 | 1.5 | 1.4 | 1.0 |
| p-Xylene | 2.6 | 2.4 | 2.3 | 1.8 | 1.8 | 3.7 |
| m-Xylene | 5.8 | 5.5 | 5.4 | 4.0 | 4.0 | |
| Trimethylbenzenes | 0.5 | 0.5 | 0.5 | 0.4 | 0.3 | 0.3 |
| Non-Volatile Aromatics | 0.5 | 0.5 | 0.5 | 0.5 | 0.5 | 0.4 |

ILLUSTRATIVE EMBODIMENT 1d

In the Illustrative Embodiments 1d and IId, the catalyst was prepared by impregnating a silica suport with an ethanol solution of Nafion XR granules, and then removing the ethanol from the solid on a rotary evaporator leaving a 6% catalyst on support composition. The support was a high surface area silica having a 1.65 ml/g pre volume, 300 m$^2$/g surface area and a 210 A average pore diameter. Ten grams of the resulting catalyst were loaded in the reactor. A stream of 100% hydrogen in a volume ratio of 2:1 with the toluene feed was maintained. The WHSV was kept at 3.6. The results are presented below in Table 2d.

Table 2d

| Time, hour | 3 | 6 | 22 | 25 | 28 | 30 |
|---|---|---|---|---|---|---|
| Temperature, ° C | 200 | 200 | 200 | 200 | 200 | 225 |
| Composition of | | | | | | |

Table 2d-continued

| Product, % w | | | | | | |
|---|---|---|---|---|---|---|
| $C_3$-$C_5$ | 0.1 | 0.1 | 0.1 | 0.1 | 0.1 | 0.2 |
| Toluene | 86.5 | 87 | 87.5 | 87.5 | 87.5 | 81 |
| Benzene | 6.4 | 6.3 | 6.0 | 6.0 | 6.0 | 9.3 |
| o-Xylene | 1.3 | 1.2 | 1.2 | 1.1 | 1.1 | 1.9 |
| p-Xylene + m-Xylene | 5.4 | 5.2 | 5.2 | 5.2 | 5.0 | 7.3 |
| Trimethylbenzenes | 0.3 | 0.3 | 0.3 | 0.3 | 0.3 | 0.4 |
| Non-Volatile Aromatics | 0.05 | 0.05 | 0.05 | 0.05 | 0.05 | 0.1 |

ILLUSTRATIVE EMBODIMENT IId

This Embodiment was conducted in a similar manner to Illustrative Embodiment Id except that the gas stream employed comprised 6% volume hydrogen an 94% volume nitrogen. The results are presented below in Table 3d.

Table 3d

| Time, hour | 4 | 25 | 46 | 68 | 76 | 96 |
|---|---|---|---|---|---|---|
| Temperature, °C | 200 | 200 | 200 | 200 | 225 | 225 |
| Composition of Product, % w | | | | | | |
| $C_3$-$C_5$ | 0.2 | 0.2 | 0.2 | 0.2 | 0.4 | 0.3 |
| Toluene | 79 | 79 | 80 | 81 | 72.5 | 90 |
| Benzene | 10 | 10.0 | 9.8 | 9.3 | 13.2 | 4.6 |
| o-Xylene | 2.1 | 2.1 | 2.0 | 1.9 | 2.7 | 1.0 |
| p-Xylene | 2.6 | 2.6 | 2.5 | 2.3 | 3.3 | 3.7 |
| m-Xylene | 5.7 | 5.5 | 5.3 | 5.0 | 7.1 |  |
| Trimethylbenzenes | 0.4 | 0.5 | 0.4 | 0.4 | 0.6 | 0.2 |
| Non-volatile Aromatics | 0.1 | 0.1 | 0.1 | 0.1 | 0.1 | — |

What is claimed is:

1. A process for the catalytic disproportionation of toluene which comprises contacting a toluene feed stream in a reaction zone at a temperature of between about 150° C and 225° C with a catalyst composition comprising a solid perfluorinated polymer catalyst supported on an inert porous carrier having an average pore diameter of between about 50 A and about 600 A in a weight ratio of catalyst to support of between about 0.1:100 and about 20:100 wherein said catalyst contains a repeating structure selected from the group of:

a)

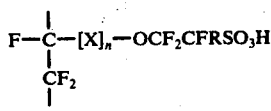

or b)

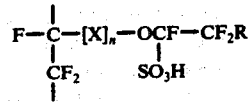

where $n$ is 0, 1 or 2; R is a radical selected from the group consisting of fluorine and perfluoroalkyl radicals having from 1 to 10 carbon atoms; and X is selected from the group consisting of:

where $m$ is an integer from 2 to 10 and Y is a radical selected from the class consisting of fluorine and the trifluoromethyl radical.

2. A process according to claim 1 wherein the weight hourly space velocity, defined as the weight per hour of toluene feed divided by the weight of catalyst (not including support) employed, varies from between about 0.5 to about 10.0 $hr^{-1}$.

3. A process according to claim 1 wherein a gas stream is added to the reaction zone in a volume ratio to the toluene feed stream of between about 0.5:1 and about 20:1 and wherein the gas stream contains between about 2% and about 95% hydrogen with the remainder being nitrogen.

4. A process according to claim 1 wherein said carrier is selected from the group consisting of alumina, silica, silica-alumina and proous glass.

5. A process according to claim 4 wherein said carrier is silica.

6. A process according to claim 1 wherein said catalyst has the general structure:

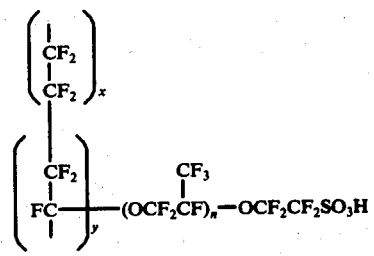

where $n$ equals 1 or 2 and the ratio of $x$ over $y$ varies from about 2 to about 50.

7. A process according to claim 1 wherein said toluene feed stream contains greater than 50% by volume toluene.

* * * * *